US00PP19400P2

(12) United States Plant Patent
Mehring-Lemper

(10) Patent No.: US PP19,400 P2
(45) Date of Patent: Nov. 4, 2008

(54) ***AGASTACHE* PLANT NAMED 'AGA 104'**

(50) Latin Name: *Agastache mexicana*
Varietal Denomination: AGA 104

(75) Inventor: Manfred Mehring-Lemper, Münden (DE)

(73) Assignee: Ernst Benary Samenzucht GmbH of Hann., Münden (DE)

( * ) Notice: Subject to any disclaimer, the term of this patent is extended or adjusted under 35 U.S.C. 154(b) by 0 days.

(21) Appl. No.: 11/881,795

(22) Filed: Jul. 27, 2007

(51) Int. Cl.
*A01H 5/00* (2006.01)

(52) U.S. Cl. ..... Plt./399

(58) Field of Classification Search ..... Plt./399
See application file for complete search history.

*Primary Examiner*—Kent L. Bell
*Assistant Examiner*—June Hwu
(74) *Attorney, Agent, or Firm*—C. A. Whealy

(57) ABSTRACT

A new and distinct cultivar of *Agastache* plant named 'AGA 104', characterized by its compact, upright and open plant habit; freely branching habit; vigorous growth habit; long inflorescences with pale orange-colored flowers; freely and continuous flowering habit; and good garden performance.

1 Drawing Sheet

Botanical designation: *Agastache mexicana.*
Cultivar denomination: 'AGA 104'.

BACKGROUND OF THE INVENTION

The present invention relates to a new and distinct cultivar of *Agastache,* botanically known as *Agastache mexicana* and hereinafter referred to by the name 'AGA 104'.

The new *Agastache* is a product of a planned breeding program conducted by the Inventor in Hann. Münden, Germany. The objective of the breeding program was to create new *Agastache* cultivars with large and dense inflorescences and attractive flower coloration.

The new *Agastache* originated from an open-pollination during the summer of 2003 in Hann. Münden, Germany, of an unnamed selection of *Agastache mexicana,* not patented, as the female, or seed, parent with an unknown selection of *Agastache mexicana* as the male, or pollen, parent. The new *Agastache* was discovered and selected by the Inventor as a single flowering plant within the progeny of the stated open-pollination in a controlled environment in Hann. Münden, Germany during the summer of 2004.

Asexual reproduction of the new *Agastache* by vegetative cuttings in a controlled environment in Hann. Münden, Germany during the winter of 2004, has shown that the unique features of this new *Agastache* are stable and reproduced true to type in successive generations.

SUMMARY OF THE INVENTION

The cultivar AGA 104 has not been observed under all possible environmental conditions. The phenotype may vary somewhat with variations in environment and cultural practices such as temperature and light intensity without, however, any variance in genotype.

The following traits have been repeatedly observed and are determined to be the unique characteristics of 'AGA 104'. These characteristics in combination distinguish 'AGA 104' as a new and distinct cultivar of *Agastache:*

1. Compact, upright and open plant habit.
2. Freely branching habit.
3. Vigorous growth habit.
4. Long inflorescences with pale orange-colored flowers.
5. Freely and continuous flowering habit.
6. Good garden performance.

Compared to plants of the female parent selection, plants of the new *Agastache* are more compact and differ in flower coloration.

Plants of the new *Agastache* can also be compared to plants of the cultivar Apricot Sprite, not patented. In side-by-side comparisons conducted in Hann. Münden, Germany, plants of the new *Agastache* and the cultivar Apricot Sprite differed in the following characteristics:

1. Plants of the new *Agastache* were larger than plants of the cultivar Apricot Sprite.
2. Plants of the new *Agastache* had longer inflorescences than plants of the cultivar Apricot Sprite.
3. Plants of the new *Agastache* had larger and lighter orange-colored flowers than plants of the cultivar Apricot Sprite.

BRIEF DESCRIPTION OF THE PHOTOGRAPHS

The accompanying colored photographs illustrate the overall appearance of the new *Agastache,* showing the colors as true as it is reasonably possible to obtain in colored reproductions of this type. Colors in the photographs may differ slightly from the color values cited in the detailed botanical description which accurately describe the colors of the new *Agastache.*

The photograph at the bottom of the sheet comprises a side perspective view of a typical flowering plant of 'AGA 104' grown in a container.

The photograph at the top of the sheet is a close-up view of a typical inflorescence of 'AGA 104'.

DETAILED BOTANICAL DESCRIPTION

The aforementioned photographs and following observations, measurements and values describe plants grown in Litchfield, Mich. during the late spring and summer and under commercial practice in a polyethylene-covered greenhouse. During the production of the plants, day temperatures ranged from 20° C. to 24° C. and night temperatures ranged from 16° C. to 18° C. After planting, plants were pinched one time. Plants had been growing for about six months when the photographs and description were taken. In the following description, color references are made to The Royal Horticultural Society Colour Chart, 1995 Edition, except where general terms of ordinary dictionary significance are used.

Botanical classification: *Agastache mexicana* cultivar AGA 104.

Parentage:

*Female, or seed, parent.*—Unnamed selection of *Agastache mexicana,* not patented.

*Male, or pollen, parent.*—Unknown selection of *Agastache mexicana,* not patented.

Propagation:

*Type.*—By vegetative cuttings.

*Time to initiate roots, summer.*—About 15 to 20 days at 22° C.

*Time to initiate roots, winter.*—About three to four weeks at 20° C.

*Time to produce a rooted young plant roots, summer.*—About four weeks at 20° C.

*Time to produce a rooted young plant roots, winter.*—About five weeks at 20° C.

*Root description.*—Fine, fibrous; 158C in color.

Plant description:

*Plant form/habit.*—Compact, upright and open plant habit; very vigorous growth habit. Freely branching habit with about ten lateral branches, each with several secondary branches; pinching enhances branching potential.

*Plant height.*—About 37 cm.

*Plant width (spread).*—About 42 cm.

*Lateral branches.*—Length: About 38 cm. Diameter: About 4 mm. Internode length: About 2.6 cm. Strength: Strong. Texture: Pubescent. Color: 147B.

Foliage description:

*Arrangement.*—Opposite, simple.

*Length.*—About 4.6 cm.

*Width.*—About 3.3 cm.

*Shape.*—Ovate to deltoid.

*Apex.*—Broadly acute.

*Base.*—Obtuse with cordate tendencies.

*Margin.*—Crenate.

*Texture, upper surface.*—Smooth, glabrous.

*Texture, lower surface.*—Pubescent.

*Venation pattern.*—Pinnate; arcuate.

*Color.*—Developing leaves, upper surface: 137A. Developing leaves, lower surface: 191A. Fully expanded leaves, upper surface: 137A; venation, 144A. Fully expanded leaves, lower surface: 191A; venation, 148D.

*Petiole length.*—About 2.3 cm.

*Petiole diameter.*—About 1.5 mm.

*Petiole texture, upper and lower surfaces.*—Pubescent.

*Petiole color, upper surface.*—144A.

*Petiole color, lower surface.*—146B.

Flower description:

*Flower type and habit.*—Numerous single bilabiate flowers arranged in verticillasters arranged in axillary long spikes. Individual flowers face mostly outward. Freely flowering habit with about 100 flowers and flower buds developing per terminal spike. Flowers not persistent.

*Natural flowering season.*—Plants flower from late June through September in the Northern Hemisphere; flowering continuous during this period.

*Inflorescence longevity on the plant.*—About three weeks.

*Fragrance.*—None detected.

*Inflorescence length.*—About 9 cm to 12 cm.

*Inflorescence width.*—About 8 cm.

*Flowers.*—Appearance: Zygomorphic; bilabiate. Length: About 4.2 cm. Diameter: About 7 mm.

*Flower buds.*—Length: About 1.7 cm. Diameter: About 2.5 mm. Shape: Obovate; curved. Color: 21A to 21B.

*Corolla.*—Petal arrangement/appearance: Bilabiate; five petals, upper two petals fused and lower three petals fused, all five petals fused at base into a tubular structure. Petal length: Upper petals, lobes: About 3 mm to 5 mm. Lower petals, lobes: About 7 mm. Petal width: Upper petals, lobes: About 3 mm. Lower petals, lobes: About 6 mm. Petal apex: Upper petals, rounded; lower petals, obovate. Petal margin: Upper petals: Entire. Lower petals: Irregularly serrate. Petal texture, upper surface: Pubescent. Petal texture, lower surface: Smooth, glabrous. Petal color: When opening, upper surface: 21B. When opening, lower surface: 21C. Fully opened, upper surface: 23B. Fully opened, lower surface: Between 23B and 23D.

*Calyx.*—Quantity/arrangement: One single calyx tube per flower; five fused sepals. Length: About 1 mm. Diameter: Less than 1 mm. Shape: Lanceolate. Apex: Acute. Margin: Entire. Texture, upper surface: Smooth, glabrous. Texture, lower surface: Pubescent. Color, upper and lower surfaces: 148B.

*Peduncles.*—Length: About 5.5 cm. Diameter: About 1.5 mm. Strength: Strong. Angle: Erect to about 45° from vertical. Texture: Pubescent. Color: 147B.

*Pedicels.*—Length: About 3 mm to 4 mm. Diameter: Less than 1 mm. Strength: Strong. Angle: About 35° to 45° from peduncle axis. Texture: Pubescent. Color: 147C.

*Reproductive organs.*—Stamens: Quantity per flower: Four. Filament length: About 3 cm. Filament color: 158A. Anther shape: Bi-lobed. Anther length: About 1 mm. Anther color: 161B. Pollen amount: Scarce. Pollen color: 155A. Pistils: Quantity per flower: One. Pistil length: About 4.4 cm. Style length: About 4.1 mm. Style color: 155A. Stigma shape: Bi-parted. Stigma color: 186D. Ovary color: 145A.

*Seed/fruit.*—Seed nor fruit production has not been observed.

Disease/pest resistance: Plants of the new *Agastache* have not been noted to be resistant to pathogens or pests common to *Agastache.*

Garden performance: Plants of the new *Agastache* have been observed to have good garden performance and to be tolerant to rain, wind and temperatures ranging from about 0° C. to 38° C.

It is claimed:

1. A new and distinct *Agastache* plant named 'AGA 104' as illustrated and described.

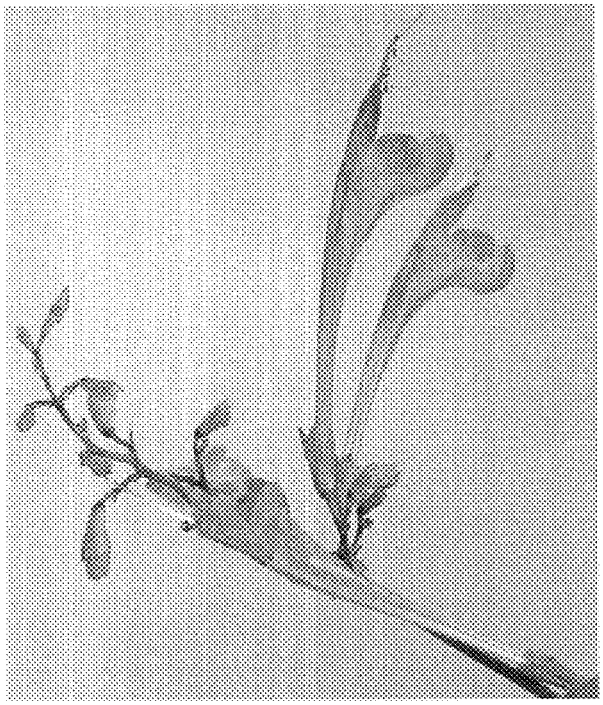
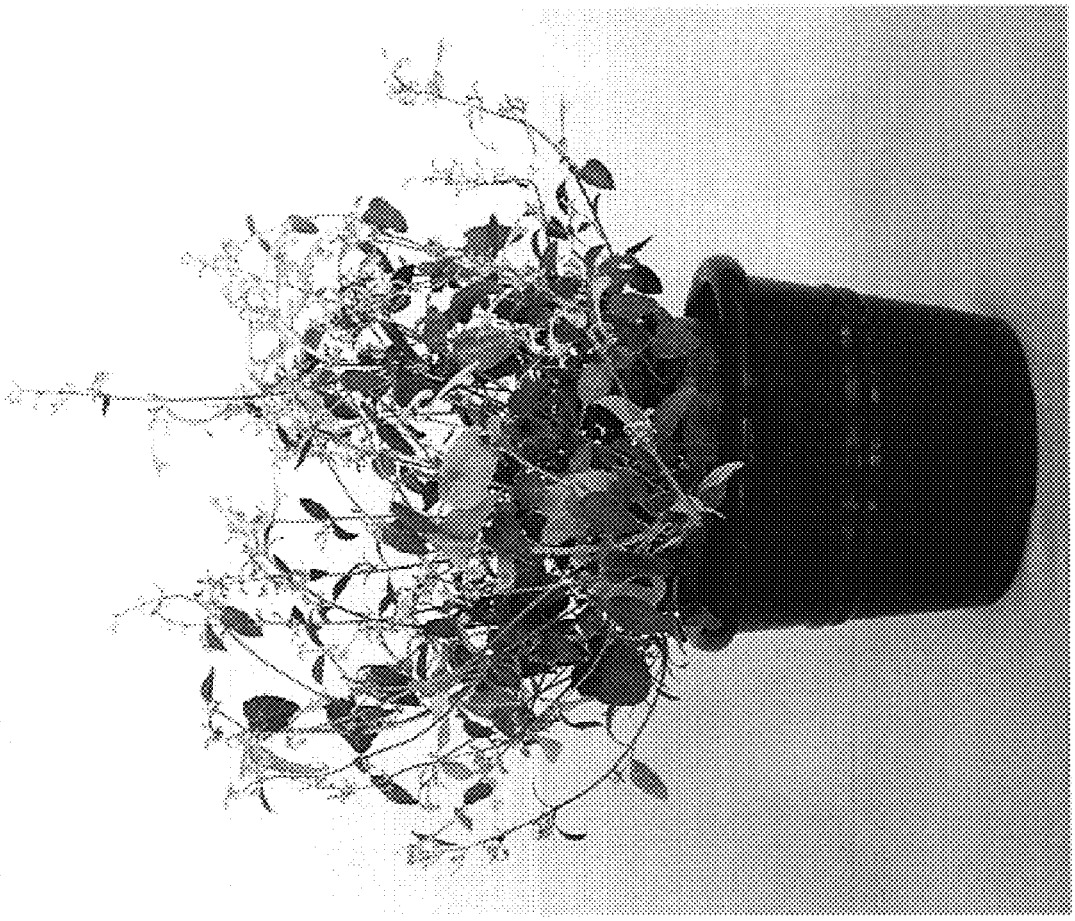

* * * * *